(12) United States Patent
Nordstedt et al.

(10) Patent No.: US 6,331,440 B1
(45) Date of Patent: Dec. 18, 2001

(54) PEPTIDE BINDING THE KLVFF-SEQUENCE OF AMYLOID-β

(75) Inventors: Christer Nordstedt, Mulhouse (FR); Jan Näslund, New York, NY (US); Johan Thyberg, Stockholm (SE); Lars O. Tjernberg, Spånga (SE); Lars Terenius, Uppsala (SE)

(73) Assignee: Karolinska Innovations AB, Stockholm (SE)

( * ) Notice: Subject to any disclaimer, the term of this patent is extended or adjusted under 35 U.S.C. 154(b) by 0 days.

(21) Appl. No.: 09/095,106

(22) Filed: Jun. 10, 1998

Related U.S. Application Data

(63) Continuation of application No. PCT/SE96/01621, filed on Dec. 9, 1996.
(60) Provisional application No. 60/009,386, filed on Dec. 29, 1995.

(30) Foreign Application Priority Data

Dec. 12, 1995 (SE) ................................................ 9504467

(51) Int. Cl.$^7$ ......................... G01N 33/566; G01N 33/53; A61K 38/08
(52) U.S. Cl. ................. 436/501; 435/7.1; 514/2; 514/17; 514/18
(58) Field of Search ...................... 435/7.1, 7.2; 436/501; 514/17, 18

(56) References Cited

U.S. PATENT DOCUMENTS

| | | | |
|---|---|---|---|
| 5,470,951 | 11/1995 | Roberts | 530/330 |
| 5,578,451 | 11/1996 | Nishimoto | 435/7.1 |
| 5,854,204 | * 12/1998 | Findeis et al. | 514/2 |

FOREIGN PATENT DOCUMENTS

| | | |
|---|---|---|
| 0584452 A1 | 3/1994 | (EP) . |
| WO94/14836 | 7/1994 | (WO) . |
| WO94/19692 | 9/1994 | (WO) . |
| WO95/08999 | 4/1995 | (WO) . |
| WO96/34887 | 11/1996 | (WO) . |

OTHER PUBLICATIONS

Tjernberg et al. J. Biol. Chem., 271, 8545–8548, Apr. 1996.*

* cited by examiner

Primary Examiner—Michael Borin
(74) Attorney, Agent, or Firm—Burns, Doane, Swecker & Mathis, L.L.P.

(57) ABSTRACT

The invention relates to compounds of formula (I) or (II), which are of interest especially for inhibition of polymerization of amyloid β peptide, as model substances for synthesis of amyloid β peptide-ligands, as tools for the identification of other organic compounds with similar functional properties and/or as ligands for detection of amyloid deposits using e.g., positron emission tomography (PET). Formula (II) is: $R_1$—A'—Y'—Leu—X'—Z'—B'—$R_2$ in which X' means any group or amino acid imparting to the compound according to formula (I) the ability to bind to the KLVFF-sequence in amyloid β peptide, or two amino acids imparting the same ability, but with the proviso that one is not proline; Y' means any amino acid; Z' means any non-acidic amino acid; A' means a direct bond or an α-amino acid bonded at the carboxyl terminal of the α-carboxy group or a di-, tri-, tetra- or pentapeptide bonded at the carboxyl terminal of the α-carboxy group; B' means a direct bond or an α-amino acid bonded at the α-nitrogen or a di-, tri-, tetra- or pentapeptide bonded at the α-nitrogen of the N-terminal α-amino acid; $R_1$ is H or —CO—$R_3$ bonded at the α-amino group of A'; $R_2$ is H, —$OR_4$ or $NR_5R_6$, all bonded to the α-carboxyl group of the α-carboxyterminal of B'; $R_3$ and $R_4$ are straight or branched carbon chain of 1–4 carbon atoms; $R_5$ and $R_6$ are independently H, alkyl, cycloalkyl, aryl or substituted aryl or together are —$(CH_2)_n$— where n is 4–5; and $R_1$ and $R_2$ together can form a hydrocarbon ring of heterocyclic ring; all α-amino acids being either D- or L-isomers.

7 Claims, 5 Drawing Sheets

PEPTIDE BINDING THE KLVFF-SEQUENCE OF AMYLOID-β

CROSS REFERENCE TO RELATED APPLICATIONS

This is a continuation of International Application No. PCT/SE96/01621, filed Dec. 9, 1996, that designates the United States and which claims priority from Swedish Application No. 9504467-3, filed Dec. 12, 1995, and U.S. Provisional Application No. 60/009,386, filed Dec. 29, 1995, which are herein incorporated by reference.

INTRODUCTION

The present invention relates to compounds, which are of special interest by their ability to bind to the KLVFF-sequence in the peptide amyloid β and to inhibit polymerization of the amyloid β peptide. The compounds according to the invention are e.g. useful as medicaments and as tools for identification of substances to be used in the treatment or prevention of amyloidosis.

BACKGROUND OF THE INVENTION

Amyloidosis is a condition which is characterized by the deposition of amyloid in organs or tissues of the human or animal body, either as a primary disease or unknown cause or secondary to chronic disease, such as tuberculosis or osteomyelitis. In addition, it has also be found that the pre-eminent neuropathological feature of Alzheimer's disease (AD), a chronic condition of brain atrophy, is the deposition of amyloid in the brain parenchyma and cerebrovasculature (D. J. Selkoe, Neuron 6, 487–498 (1991); D. J. Selkoe, Annu. Rev. Cell Biol. 10, 373–403 (1994)).

The basic component of such amyloid is a peptide termed amyloid β, or Aβ (G. C. Glenner, C. W. Wong, Biochem. Biophys. Res. Commun. 120, 885–890 (1984)). It is a 40 to 42 amino acids long proteolytic fragment of the Alzheimer amyloid precursor protein (APP), a protein expressed in most tissues (J. Kang, et al., Nature 325, 733–736 (1987)). Genetic and neuropathological studies provide strong evidence for a central role of Aβ in the pathogenesis of AD, but the pathophysiological consequences of the amyloid deposition are still unclear. However, it has been suggested that Aβ polymers and amyloid are toxic to neurons, either directly or indirectly, and hence cause neurodegeneration (C. Behl, J. B. Davis, R. Lesley, D. Schubert, Cell 77, 817–827 (1994); D. T. Loo, et al., ibid 90, 7951–7955 (1995)).

The amyloid associated with Alzheimer's disease (AD) consists of thin fibrils of polymerized Aβ. A rational pharmacological approach for the prevention of amyloidogenesis would therefore be to use drugs that specifically interfere with Aβ—Aβ interaction and polymerization. Previous studies showed that Aβ polymerization in vivo and in vitro is a highly specific process, which probably involves an interaction between binding sequences in the Aβ peptide (J. N äslund, et al., Proc. Natl. Acad. Sci. USA 91, 8378–8382 (1994); J. Näslund, et al., Biochem. Biophys. Res. Commun. 204, 780–787 (1994)).

Wood et al (S. J. Wood, R. Wetzel, J. D. Martin, M. R. Hurle, Biochemistry 34, 724–730 (1995)) suggest that amino acid residues within or close to Aβ-16-20 are important for the adoption of the correct β-pleated sheet structure of Aβ and show that amino acids 17–23 in the amyloid β peptide (Aβ) are essential for fibril formation and probably make up the β-sheet core of the fibrils. In addition, Wood et al. have investigated the ability of their peptides to form amyloid fibrils in a solution containing solely the mutated or the wild-type peptide. However, no method or principle which makes it possible to inhibit Aβ of wild type from forming amyloid fibrils is devised and no use of the peptides as medicaments is suggested.

WO 95/08999 relates to amelioration of amnesia in Alzheimer's disease caused by deposition of amyloid β protein. Three peptides are disclosed, which overcome the amnestic effects of β-12-28, a peptide homologous to Aβ. In addition, WO 95/08999 describes the screening of several other peptides, which were neither significantly amnestic nor memory enhancing, of which one is KLVFF, SEQ. NO. 15 of the sequence listing therein.

In EP 0 584 452, novel amyloid precursor proteins and the sequences thereof are disclosed. Peptide sequences that comprise KLVFF are revealed. However, neither binding to amyloid β peptide nor any inhibition of the polymerization thereof is suggested.

SUMMARY OF THE INVENTION

Thus, the polymerization of the amyloid β peptide (Aβ) into amyloid fibrils is a critical step in the pathogenesis of Alzheimer's disease.

In vitro and in vivo studies of Aβ have shown that the Aβ molecules interact with a high degree of specificity during polymerization and fibril formation. It was assumed that ligands which bind to recognition sequences would be capable of inhibiting Aβ polymerization and possibly also dissolve preformed Aβ polymers in situ. The strategy in finding such Aβ ligands was to identify critical binding regions in Aβ and, based on their sequences, develop a compound capable of blocking the Aβ—Aβ binding.

According to the invention, it was hypothesized that compounds capable of binding to regions in the Aβ-molecule critical for its polymerization might inhibit amyloid fibril formation, as described in more detail below.

According to the invention, it has now been found that the Lys-Leu-Val-Phe-Phe (KLVFF) (SEQ ID NO:1) sequence in Aβ is necessary for polymerization to occur. Peptides incorporating this sequence bind to Aβ and are capable of blocking the fibril formation of Aβ-1-40 and are therefore potentially useful as drugs.

In addition, compounds have been found, which 1) are capable of binding to full-length Aβ,
2) are capable of blocking Aβ fibril formation and
3) do not form fibrils by themselves.

In addition, it has also been found that alanine-substituted Aβ-1-28 (Ala at position 16,17,20), in contrast to wild-type Aβ-1-28, does not form fibrils.

Thus, it was concluded that the Lys-Leu-Val-Phe-Phe (16–20) motif serves as a structural basis for the development of peptide and non-peptide agents aimed at inhibiting amyloidogenesis in vivo. This is a novel finding and the compounds are of utmost interest as being useful as drugs for Alzheimer's disease.

Further, the findings according to the invention are even more surprising on the basis of what was concluded from WO 95/08999 mentioned above. In WO 95/08999, it was concluded that KLVFF is not a potential candidate for the development of substances that can antagonize binding of Aβ and thus attenuate symptoms and progression of AD. Even though the teaching of said WO publication indicates the opposite, according to the present invention, it has now been found that KLVFF on the contrary is most useful for the development of new compounds defined by Formula (I) and (II) below.

DETAILED DESCRIPTION OF THE INVENTION

The present invention relates to compounds which are able to bind to the Lys-Leu-Val-Phe-Phe-sequence, or KLVFF-sequence, in the peptide amyloid β. More specifically, the compounds according to the invention are defined by their formula (I):

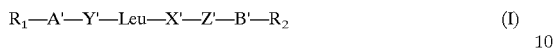

in which
- X' means any group or amino acid imparting to the compound of formula (I) the ability to bind to the KLVFF-sequence in amyloid β peptide, or two amino acids imparting the same ability, but with the proviso that one is not proline;
- Y' means any amino acid;
- Z' means any non-acidic amino acid;
- A' means a direct bond or an α-amino acid bonded at the carboxyl terminal of the α-carboxy group or a di-, tri-, tetra- or pentapeptide bonded at the carboxyl terminal of the α-carboxy group;
- B' means a direct bond or an α-amino acid bonded at the α-nitrogen or a di-, tri-, tetra- or pentapeptide bonded at the α-nitrogen or the N-terminal α-amino acid;
- $R_1$ is H or —CO—$R_3$ bonded at the α-amino group of A';
- $R_2$ is H, —OR$_4$ or NR$_5$R$_6$, all bonded to the α-carboxyl group of the α-carboxyterminal of B';
- $R_3$ is a straight or branched carbon chain of 1–4 carbon atoms;
- $R_4$ is a straight or branched carbon chain of 1–4 carbon atoms;
- $R_5$ and $R_6$ independently are H, alkyl, cycloalkyl, aryl or substituted aryl or together are —(CH$_2$)$_n$—, where n is 4–5;
- $R_1$ and $R_2$ together can form a hydrocarbon ring or heterocyclic ring; and
- all the α-amino acids can be wither D- or L-isomers;
- with the proviso that (I) is not Lys-Leu-Val-Phe-Phe.

With alkyl is preferably meant a chain of 4 or less carbon atoms, e.g. methyl, ethyl, propyl or butyl.

With cycloalkyl is preferably meant a ring of 3, 4, 5 or 6 carbon atoms.

Aryl preferably means a phenyl group, which can be substituted, preferably by a methyl, ethyl, propyl or butyl group, an amino or a methoxy, ethoxy, propoxy or butoxy group.

In a preferred embodiment of the present invention, the compound exhibits an ability to inhibit polymerization of amyloid β peptide.

In one embodiment of the invention, all the amino acids of the compound are D-isomers.

In one embodiment of the invention, Y' is Lys, and in a particular embodiment of the invention, Z' is Phe, resulting in a compound of the following formula:

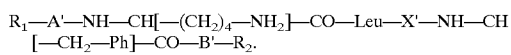

In an alternative embodiment of the invention, Y' is Phe. Preferred are compounds, wherein X' is Val-Val.

In one embodiment of the present aspect of the invention, $R_1$ is acetyl.

In an alternative embodiment of the invention, $R_1$ is H. According to another embodiment, $R_2$ is H. Alternatively, $R_1$ and $R_2$ are both H.

A second aspect of the present invention is the use of a compound of formula:

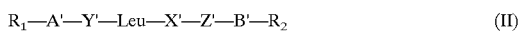

in which
- X' means any group or amino acid imparting to the compound of formula (II) the ability to bind to the KLVFF-sequence in amyloid β peptide, or two amino acids imparting the same ability, but with the proviso that one is not proline;
- Y' means any amino acid;
- Z' means any non-acidic amino acid;
- A' means a direct bond or an α-amino acid bonded at the carboxyl terminal of the α-carboxy group or a di-, tri-, tetra- or pentapeptide bonded at the carboxyl terminal of the α-carboxy group;
- B' means a direct bond or an α-amino acid bonded at the α-nitrogen or a di-, tri-, tetra- or pentapeptide bonded at the α-nitrogen of the N-terminal α-amino acid;
- $R_1$ is H or —CO—$R_3$ bonded at the α-amino group of A';
- $R_2$ is H, —OR$_4$ or NR$_5$R$_6$, all bonded to the α-carboxyl group of the α-carboxyterminal of B';
- $R_3$ is a straight or branched carbon chain of 1–4 carbon atoms;
- $R_4$ is a straight or branched carbon chain of 1–4 carbon atoms;
- $R_5$ and $R_6$ independently are H, alkyl, cycloalkyl, aryl or substituted aryl or together are —(CH$_2$)$_n$— where n is 4–5;
- $R_1$ and $R_2$ can together form a hydrocarbon ring or heterocyclic ring; and
- all the α-amino acids can be either D- or L-isomers;

for inhibition of polymerization of amyloid β peptide, as a model substance of synthesis of amyloid β peptide-ligands for inhibition of polymerization of amyloid β peptide, as a tool for the identification of other organic compounds with similar functional properties or as ligand for detection of amyloid deposits using e.g. positron emission tomography (PET).

With alkyl is preferably meant a chain of 4 or less carbon atoms, e.g. methyl, ethyl, propyl or butyl.

With cycloalkyl is preferably meant a ring of 3, 4, 5 or 6 carbon atoms.

Aryl preferably means a phenyl group, which can be substituted, preferably by a methyl, ethyl, propyl, or butyl group, an amino or a methoxy, ethoxy, propoxy or butoxy group.

In one embodiment of this second aspect of the invention, a compound is used, wherein all the amino acids are D-isomers.

In a particular embodiment of this aspect of the invention, Y' is Lys. A particular embodiment is when Z' is Phe, resulting in a compound of the following formula:

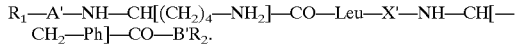

In an alternative embodiment, a compound is used, wherein Y' is Phe while Z' is any non-acidic amino acid.

In a preferred embodiment of this aspect of the invention, a compound is used, wherein X' is Val-Val.

In one embodiment of the use according to the invention, $R_1$ is acetyl. Alternatively, $R_1$ and/or $R_2$ are H.

Yet another aspect of the present invention is a compound according to the invention for use as a medicament.

Also claimed is the use of a compound, preferably of the formula (I) or (II), which is able to bind to the KLVFF-sequence in amyloid β peptide and which has the ability to inhibit polymerization of amyloid β peptide, for the manufacture of a medicament for the treatment or prevention of amyloidosis, especially in the treatment or prevention of Alzheimer's disease associated with amyloidosis, for the treatment or prevention of demens in patients with Down's syndrome, for the treatment or prevention of Hereditary cerebral hemorrhage with amyloidosis (Dutch type) or for the prevention of fibril formation of human amyloid protein.

Further, a last aspect of the present invention is a composition comprising a compound according to formula II and optionally a ligand capable of binding or interacting with the compound according to formula II and a carrier.

Said composition can e.g. be adapted for injection in a liquid carrier or for oral administration in a tablet or capsule.

Carriers are known for persons skilled in the art.

For clarification the following definitions are given: K is lysine (Lys), L is leucine (Leu), V is valine (Val), F is phenylalanine (Phe), A is alanine (Ala) and E is glutamic acid (Glu).

As used herein, "any group giving the compound according to formula (I) the ability to bind to the KLVFF-sequence in the amyloid β peptide" means that this group gives the compound a structure, which can fulfil the requirements given in claim 1.

The hydrocarbon ring or heterocyclic ring has preferably 4–6 atoms, preferably C, N and S.

EXPERIMENTAL

EXAMPLE 1 a) Ten-mers corresponding to consecutive sequences of Aβ-1-40 were synthesized on a filter matrix using the SPOT-technique (the peptides were synthesized essentially as described by Frank [R. Frank, *Tetrahedron* 42, 9217–9232 (1992)]. Briefly, a spacer corresponding to 2 molecules of β-alanine was coupled to cellulose membranes (Whatman 1Chr). The peptides were synthesized on these derivatized membranes using Fmoc protected and pentafluorophenyl-activated amino acids (AMS Biotechnology) dissolved in N-methylpyrrolidone. Coupling efficiency was monitored using bromophenol blue.). We synthesized the thirty-one possible 10-mers of the Aβ-1-40. Peptide no. 1 corresponds to amino acids 1–10, peptide no. 2 to amino acids 2–11 etc. The filter-bound peptides were incubated with radioactive Aβ-1-40. Following washing of the filter in high-salt buffer, bound radioactivity was estimated by autoradiography and densitometry. Following blocking with 0.05% Tween-20 in Tris-buffered saline (TBS), the filter was incubated in the presence of 20 μM $^{125}$I-labelled Aβ-1-40 at 20° C. for 12 h in TBS, pH 7.3, supplemented with 1% bovine serum albumin. The filter was then washed repeatedly in the same buffer containing 0.5 M NaCl and dried. Radioactivity bound to the filter was visualized by autoradiography and quantitated using a densitometer.

b) Peptide no. 11 (EVHHQKLVFF) and indicated N- and C-terminal truncated fragments were synthesized using the same technique as described above and analyzed for affinity to $^{125}$I-labelled Aβ-1-40.

c) Sensorgram from BIAcore 2000. Aβ-1-40, at three different concentrations in running buffer, pH 7.4. Aβ-1-40 was injected during 10 minutes over a sensor-chip derivatized with the peptide KLVFF-βA-βA-C.

d) Each amino acid residue in KLVFF was systematically replaced with A and analyzed for affinity to $^{125}$I-labelled Aβ-1-40. Non-specific interactions have been compensated for by subtracting the signal from a surface derivatized with C alone.

Figure 1B:
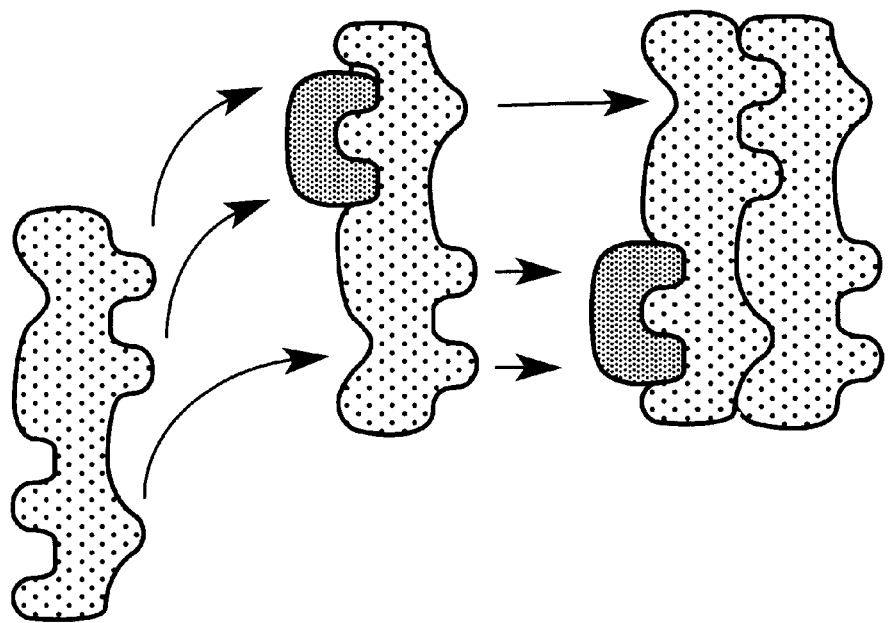
FIGS. 1A and B. Aβ- amyloid polymerization.
Figure 1A:
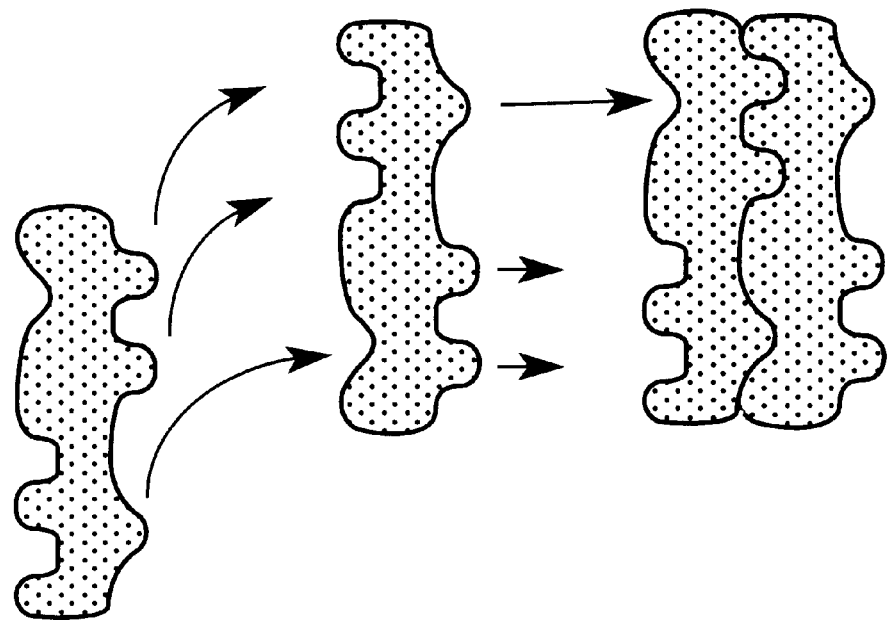
Figure 2A:
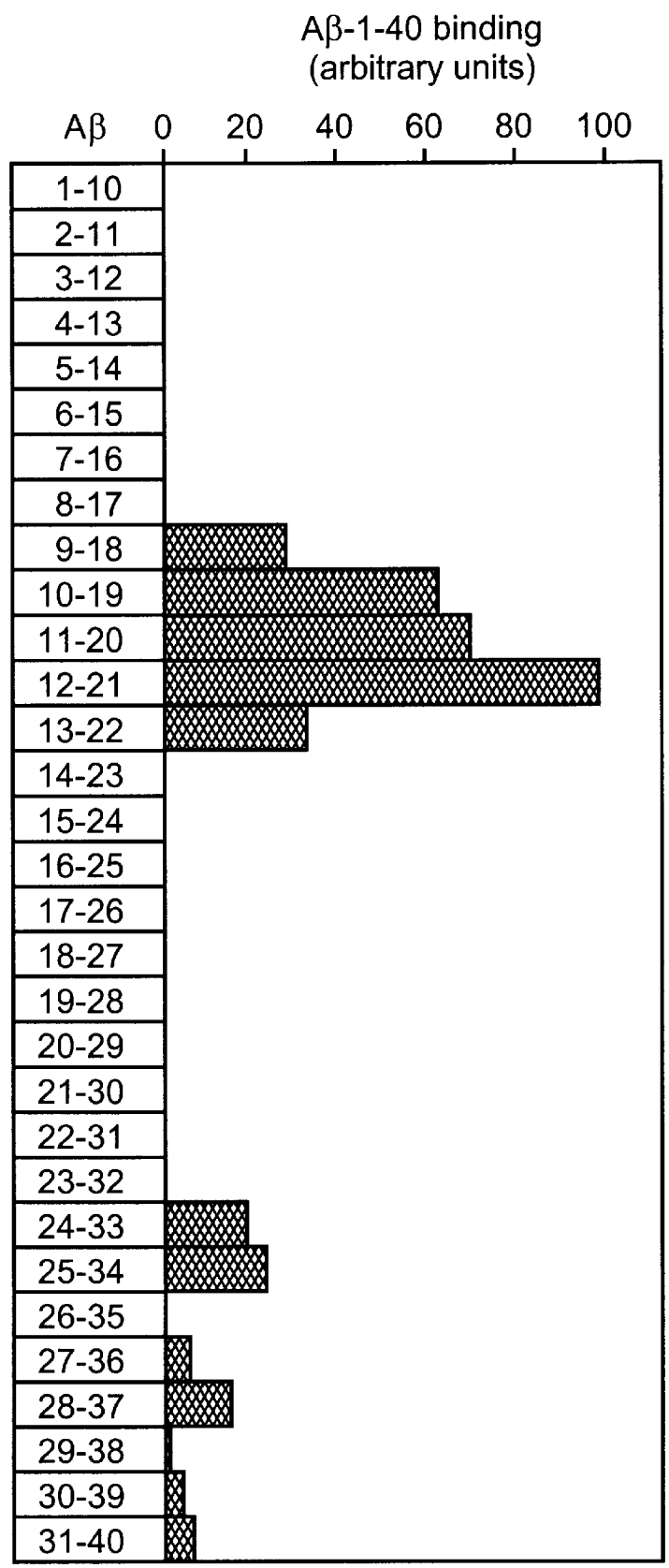
FIG. 2A. Ten-mers corresponding to consecutive sequences of Aβ-1-40. Radioactivity bound to the filter was detected by autoradiography and quantified by densitometry.
Figure 2B:
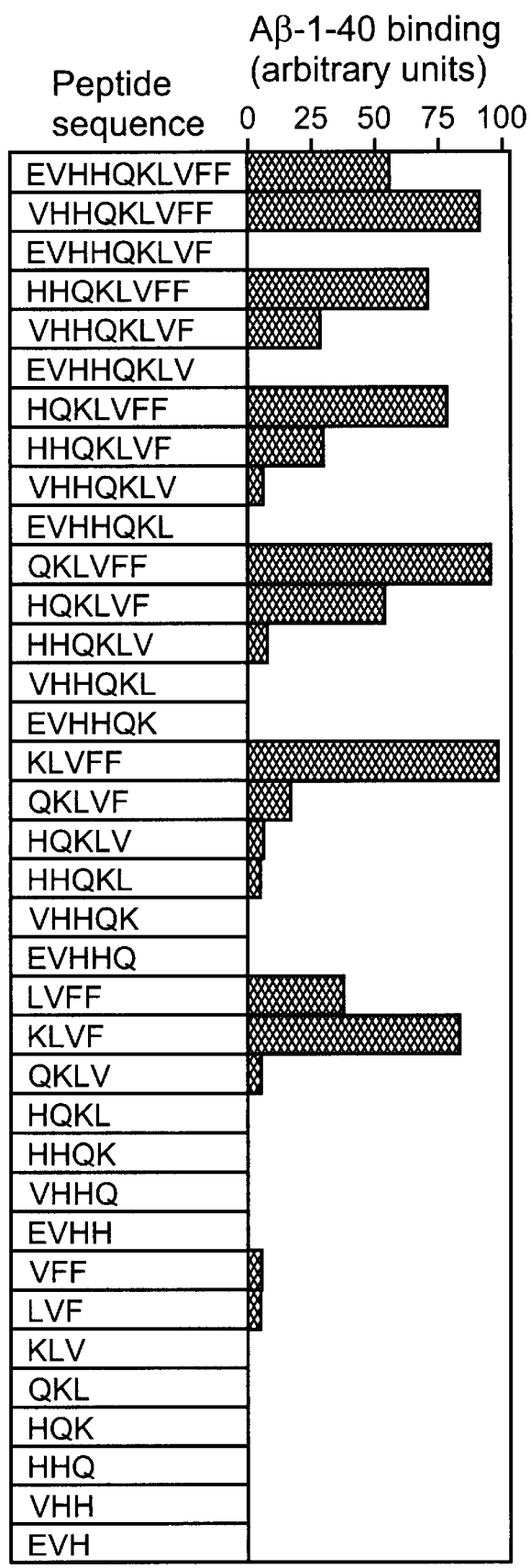
FIG. 2B. (SEQ ID NOS.: 1, 2 and 5–38) EVHHQKLVFF and N and C-terminal truncated fragments were synthesized and analyzed for affinity to $^{125}$I-labelled Aβ-1-40.
Figure 2C:
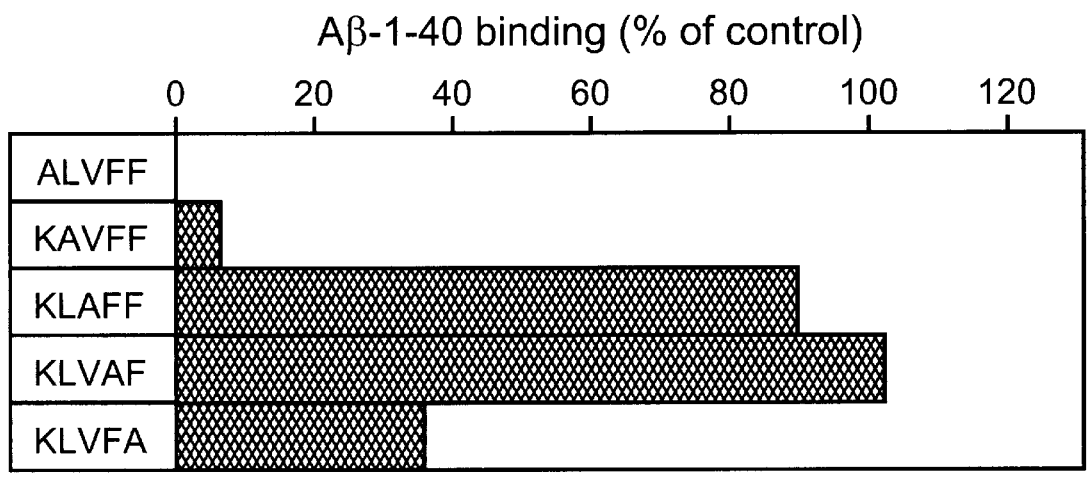
FIG. 2C. (SEQ ID NOS.: 39–43) Each amino acid residue in KLVFF was systematically replaced with Ala and analyzed for affinity to $^{125}$I-labelled Aβ-1-40.
Figure 2D:
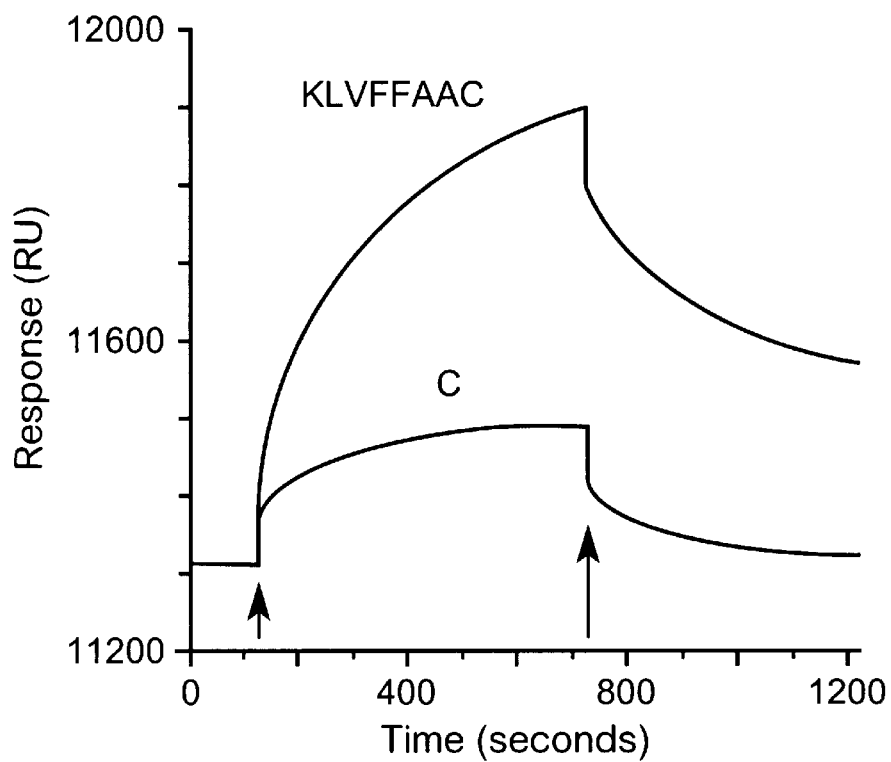
FIG. 2D. (SEQ ID NO.: 44) Sensorgram from surface plasmon resonance spectroscopy (BIAcore 2000).

Results a) The measured binding should be interpreted as semiquantative, since the coupling efficiency and therefore the amount of peptide per spot may vary. A region located in the central part of Aβ (Aβ-9-18 to Aβ-13-22) displayed prominent binding of radioactive Aβ-1-40. Another binding region was the hydrophobic C-terminus of the molecule (D. Burdick, et al, *J. Biol. Chem.* 267, 546–554 (1992)) but binding here was considerably weaker (FIG. 2A).

b) Being located in the centre of the binding region, peptide no. 11 (corresponding to Aβ-11-20) was selected for further studies. This peptide, as well as N- and C-terminal fragments thereof, were synthesized using the same technique as described previously. The shortest peptide still displaying high Aβ binding capacity had the sequence KLVFF, corresponding to amino acids 16–20 of Aβ (FIG. 2B). By systematically substituting the amino acid residues in the KLVFF sequence with alanine, we found that the first, second and fifth residues (i.e. KLXXF) were critical for binding (FIG. 2C).

c) The interaction between soluble Aβ-1-40 and immobilized KLVFF was monitored in real-time (FIG. 2D) using surface plasmon resonance spectroscopy (BIAcore, Pharmacia) (BIAcore 2000 (Pharmacia Biosensor AB, Sweden) was used for real-time studies based on surface plasmon resonance spectroscopy. The peptide was immobilized using thiol coupling. The running buffer consisted of 10 mM HEPES, 0.15 M NaCl, 3.4 mM EDTA and 0.05% surfactant P20 as described. [U. Jansson, M. Malmqvist, *Adv. Biosens.* 2, 291–336 (1992)]). The binding was not saturable, indicating that Aβ-1-40 bound to immobilized KLVFF could interact with other Aβ-1-40 molecules in a polymerization reaction.

d) AA served as linker between the active peptide and the chip (upper trace) and cysteine along, indicating non-specific binding, (C) as control (lower trace). Arrows indicate start and stop of injection (FIG. 2D).

EXAMPLE 2

To investigate if the KLXXF (SEQ ID NO.: 3) motif was required for Aβ polymerization, we synthesized Aβ-1-28, a well-studied Aβ fragment that readily forms amyloid fibrils (D. A. Kirschner, et al., *Proc. Natl. Acad. Sci. USA* 84, 6953–6957 (1987); C. J. Barrow, M. G. Zagorski, *Science*

253, 179–82 (1991); C. Nordstedt, et al., *J. Biol. Chem.* 269, 30773–30776 (1994)) and mutated Aβ-1-28 where the KLVFF sequence was substituted with AAVFA (SEQ ID NO.: 4) (Aβ-1-28 $^{AAVFA}$).

Figure 3A:
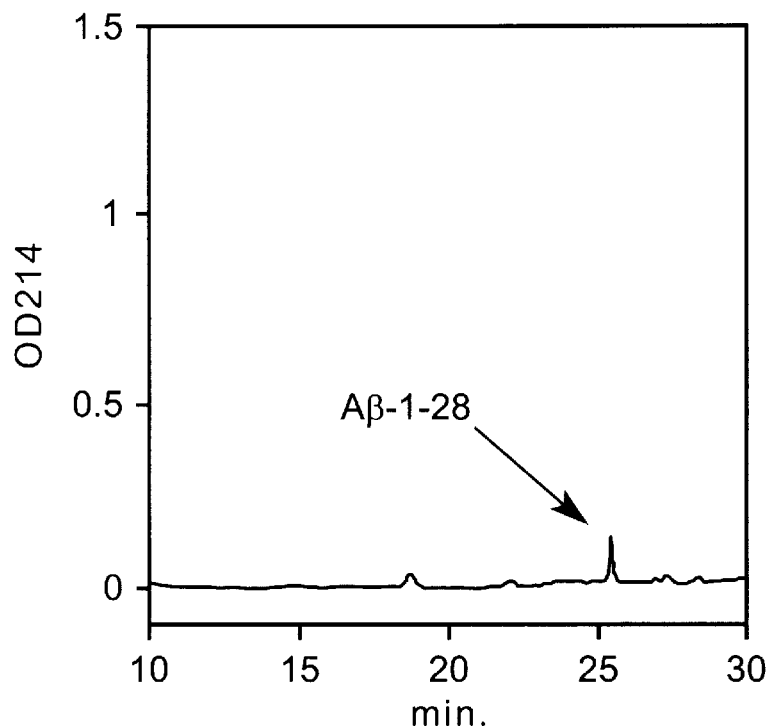
FIGS. 3A and B. Content of non-aggregated peptide in the supernatants from incubations of wild-type and Ala-substituted Aβ-1-28 as analyzed by HPLC.
Figure 3B:
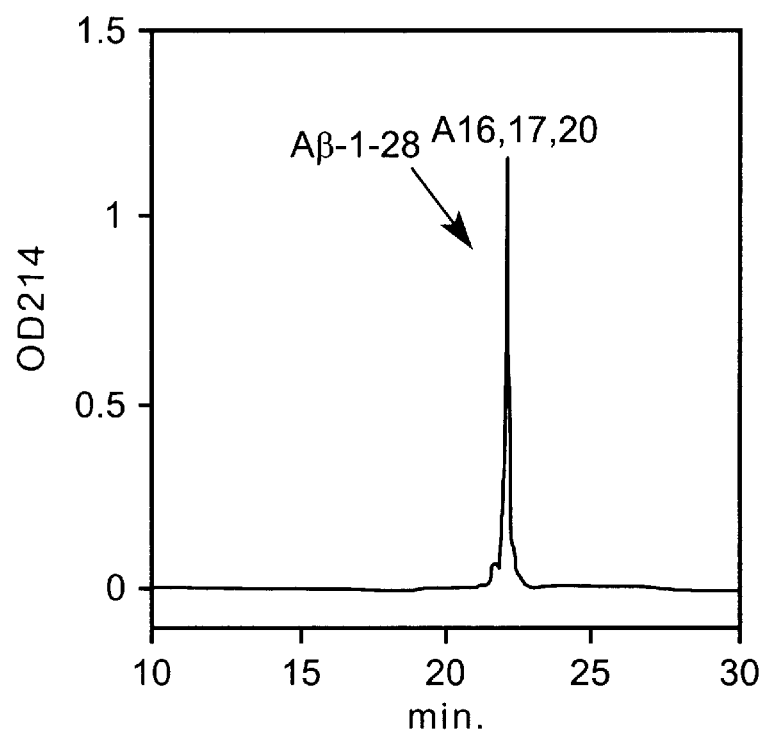

Aβ-1-28 (FIG. 3A) and Aβ-1-28$^{AAVFA}$ (FIG. 3B) were incubated at 200 µM in TBS for 24 h at 37° C. in a shaking water bath. After incubation, the tubes were centrifuged at 20,000 g for 20 min and the content of non-aggregated peptide in the supernatants (FIGS. 3A, B) was analyzed using an established C4 RPLC system (12) whereas the aggregated peptides in the pellets were analyzed by electron microscopy after adsorption to formvar-coated grids and negative staining with 2% uranyl acetate in water.

Results

Following incubation at a concentration of 200 µM for 24 h at 37° C., Aβ-1-28 aggregated (FIG. 3A) and formed large fibril bundles, whereas Aβ-1-28$^{AAVFA}$ almost completely failed to aggregate (FIG. 3B) and only formed a few dispersed fibrils.

EXAMPLE 3

Aβ-1-40 was incubated at 100 µM in TBS for 48 h at 37° C. in a shaking water bath, either along or together with 100 µM AcKLVFFNH$_2$. The polymerized material was adsorbed to formvar-coated grids and negatively stained with 2% uranyl acetate in water.

Results

Incubation of synthetic Aβ-1-40 at 100 µM for 48 h at 37° C. in a physiological buffer led to polymerization and formation of amyloid fibrils arranged in parallel in densely packed bundles, as previously shown (C. Nordstedt, et al., *J. Biol. Chem.* 269, 30773–30776 (1994)). When Aβ-1-40 was coincubated with AcQKLVFFNH$_2$ at equimolar concentrations, this type of fibrils did not form. Instead, only a few occasional fibrils embedded in a diffuse background of small rod-like aggregates, similar to those formed by AcQKLVFFNH$_2$ itself, could be detected.

EXAMPLE 4

The peptides were synthesized essentially as described by Frank (Frank R. 1992, Tetrahedron 42:9217–9232). Briefly, a spacer corresponding to 2 molecules of β-alanine was coupled to cellulose membranes (Whatman XX). The peptides were synthesized on these derivatized membranes using Fmoc protected and pentafluorophenyl-activated amino acids (AMS biotechnology) dissolved in N-methylpyrrolidone. Coupling efficiency was monitored using bromphenol blue.

Results

The KLXXF motif in the Aβ molecule is not only critical for polymerization and fibril formation. During non-amyloidogenic processing of APP, the molecule is cleaved between amino acid residues $K^{16}$ and $L^{17}$ (F. S. Esch, et al., *Science* 248, 1122–1124 (1990)), leading to the formation of a fragment of Aβ termed p3 and corresponding to Aβ-17-40 or Aβ-17-42 (C. Haass, A. Y. Hung, M. G. Schlossmacher, D. B. Teplow, D. J. Selkoe, *J. Biol. Chem.* 268, 3021–3024 (1993)). Through this metabolic pathway the present binding sequence is disrupted. This may explain why p3 is not capable of forming amyloid in vitro or in vivo (J. Näslund, et al., *Proc. Natl. Acad. Sci. USA* 91, 8378–8382 (1994); J. Näslund, et al., *Biochem. Biophys. Res. Commun.* 204, 780-14 787 (1994)). The KLXXF motif is highly sequence specific. The most apparent example of this is the finding that substitution of a single amino acid leads to virtually complete loss of Aβ binding capacity.

EXAMPLE 5

In an additional series of experiments, it was demonstrated that KLVFF binds stereo specifically to the homologous sequence in Aβ (i.e. Aβ-16-20). By screening combinatorial pentapeptide libraries exclusively composed of D-amino acids (lowercase) with labelled KLVFF, several ligands with a motif containing phenylalanine (f) in the second and leucine (l) in the third position were identified (e.g. lflrr). By using a short peptide in the screening, known to bind to a region in Aβ critical for its polymerization (i.e. KLVFF), the risk of identifying D-pentapeptides that interact with nonrelevant regions in Aβ (N- or C-terminal to Aβ-16-20) was eliminated. Like KLVFF, the D-amino acid ligands were found not only to bind to Aβ but also to inhibit amyloid fibril formation. Since peptides built up of D-amino acids are resistant to proteolytic degradation, these ligands may be beneficial for inhibition of amyloidogenesis in vivo. The results further indicate that KLVFF will be useful in the identification of small organic molecules (e.g. by screening of substance libraries) with the ability to bind to Aβ in this relevant region and inhibit amyloid fibril formation (candidate drugs for the treatment of Alzheimer disease and other related amyloidoses).

Discussion and Conclusion

Previous studies of putative inhibitors of amyloid fibril formation showed that cyclodextrins (P. Camilleri, N. J. Haskind, D. R. Howlett, *FEBS Lett.* 341, 256–258 (1994)) and Congo red (A. Lorenzo, H. Yankner, *Proc. Natl. Acad. Sci. USA* 91, 12243–12247 (1994)) may have such properties. The usefulness of these molecules as lead or model substances in development of anti-Alzheimer amyloid drugs is, however, compromised by their relative lack of specificity. Cyclodextrins have primarily been used to increase the solubility of a wide range of lipophilic drugs and it is unlikely that they would display any specificity for Aβ in vivo. Congo red, which is used in histochemistry to detect amyloid, binds to a wide array of non-Aβ amyloids as well as to other proteins with a high content of β-pleated sheet structures (W. G. Turnell, J. T. Finch, *J. Mol. Biol.* 227, 1205–1223 (1992)).

Due to the extreme insolubility of amyloid, strong chaotropic agents or potent organic solvents are required for its dissolution (C. L. Masters, et al., *Proc. Natl. Acad. Sci. USA* 82, 4245–4249 (1985)), the concept of dissolving amyloid deposits in situ under physiological conditions may seem futile. However, the bulk of the individual molecules in amyloid are probably not joined by covalent bonds and the deposition of Aβ into amyloid is, at least at some stages, a dynamic and reversible process (J. E. Maggio, et al., ibid., 89, 5462–5466 (1992)). Hence, a molecule capable of binding to a site in the Aβ molecule that is critical for fibril formation with an affinity higher than native Aβ should have reasonable changes to inhibit amyloid growth and may be also specifically dissolve amyloid fibrils.

In conclusion, we have identified an Aβ sequence, KLVFF, which is required for amyloid fibril formation. The KLVFF peptide may serve as a model substance for the synthesis of non-peptide Aβ-ligands that interfere with the polymerization of Aβ molecules.

Previous studies suggested that amino acid residues within or close to Aβ-16-20 are important for the adoption of the correct β-pleated sheet structure of Aβ (18) and the proteolytic processing of its precursor (14).

We have now shown that this region harbors at least one binding sequence required for the polymerization of Aβ into amyloid fibrils. It was also demonstrated that short peptides incorporating Aβ-16-20 can function as ligands that bind to Aβ and inhibit the formation of amyloid fibrils. Since these peptide ligands are relatively small, they are amenable for identification of other organic molecules with similar functional properties. Non-peptide homologues of KLVFF should be useful as pharmacological drugs for the treatment of Alzheimer's disease in the future.

We claim:

1. A method for identifying an organic compound which is capable of inhibiting the polymerization of an amyloid beta peptide, wherein said amyloid beta peptide contains the KLVFF sequence comprising the following steps:

(i) producing a first reaction composition comprising an amyloid beta peptide, wherein said amyloid beta peptide contains the KLVFF sequence and further comprising a first compound having the formula:

K—L—X—F    (I)

wherein X is one or two amino acid residues imparting to the compound of formula (I) the ability to bind to the KLVFF sequence in amyloid beta peptide with the proviso that X is not proline;

wherein said first compound inhibits the polymerization of said amyloid beta peptide contained in said composition based on its binding to the amyloid beta peptide;

(ii) producing a second reaction composition containing amyloid beta peptide which contains the KLVFF sequence, and further containing said first compound as recited in (i), wherein said second reaction composition is identical to the first reaction composition except for the additional presence of a second compound, which is an organic compound that is being screened for whether said organic compound binds to KLVFF in amyloid beta peptide;

(iii) comparing the inhibition of polymerization of amyloid beta peptide in said first and second reaction compositions by the first compound; and (iv) determining whether the second compound inhibits the polymerization of an amyloid beta peptide containing the KLVFF sequence.

2. The method of claim 1, wherein X is Val.

3. The method of claim 1, wherein X is VAL-VAL.

4. The method of claim 3, wherein the first compound is KLVF.

5. The method of claim 1, wherein the first compound is KLAFF, KLVFF, KLVVF, or KLVAF.

6. The method of claim 1, wherein the amino acids of said first compound are all L-isomers.

7. The method of claim 1, wherein the amino acids of said first compound are all D-isomers.

* * * * *

```
                             SEQUENCE LISTING

<160> NUMBER OF SEQ ID NOS: 44

<210> SEQ ID NO 1
<211> LENGTH: 5
<212> TYPE: PRT
<213> ORGANISM: Amyloidosis

<400> SEQUENCE: 1

Lys Leu Val Phe Phe
 1               5

<210> SEQ ID NO 2
<211> LENGTH: 10
<212> TYPE: PRT
<213> ORGANISM: Amyloidosis

<400> SEQUENCE: 2

Glu Val His His Gln Lys Leu Val Phe Phe
 1               5                  10

<210> SEQ ID NO 3
<211> LENGTH: 5
<212> TYPE: PRT
<213> ORGANISM: Amyloidosis
<220> FEATURE:
<221> NAME/KEY: PEPTIDE
<222> LOCATION: (3)..(4)
<223> OTHER INFORMATION: Amino acids 3 and 4 are Xaa wherein Xaa = any
      group or amino acid.

<400> SEQUENCE: 3

Lys Leu Xaa Xaa Phe
 1               5

<210> SEQ ID NO 4
<211> LENGTH: 5
<212> TYPE: PRT
<213> ORGANISM: Amyloidosis

<400> SEQUENCE: 4

Ala Ala Val Phe Ala
 1               5

<210> SEQ ID NO 5
<211> LENGTH: 6
<212> TYPE: PRT
<213> ORGANISM: Amyloidosis

<400> SEQUENCE: 5

Gln Lys Leu Val Phe Phe
 1               5

<210> SEQ ID NO 6
<211> LENGTH: 9
<212> TYPE: PRT
<213> ORGANISM: Amyloidosis

<400> SEQUENCE: 6

Val His His Gln Lys Leu Val Phe Phe
 1               5
```

<210> SEQ ID NO 7
<211> LENGTH: 9
<212> TYPE: PRT
<213> ORGANISM: Amyloidosis

<400> SEQUENCE: 7

Glu Val His His Gln Lys Leu Val Phe
 1               5

<210> SEQ ID NO 8
<211> LENGTH: 8
<212> TYPE: PRT
<213> ORGANISM: Amyloidosis

<400> SEQUENCE: 8

His His Gln Lys Leu Val Phe Phe
 1               5

<210> SEQ ID NO 9
<211> LENGTH: 8
<212> TYPE: PRT
<213> ORGANISM: Amyloidosis

<400> SEQUENCE: 9

Val His His Gln Lys Leu Val Phe
 1               5

<210> SEQ ID NO 10
<211> LENGTH: 8
<212> TYPE: PRT
<213> ORGANISM: Amyloidosis

<400> SEQUENCE: 10

Glu Val His His Gln Lys Leu Val
 1               5

<210> SEQ ID NO 11
<211> LENGTH: 7
<212> TYPE: PRT
<213> ORGANISM: Amyloidosis

<400> SEQUENCE: 11

His Gln Lys Leu Val Phe Phe
 1               5

<210> SEQ ID NO 12
<211> LENGTH: 7
<212> TYPE: PRT
<213> ORGANISM: Amyloidosis

<400> SEQUENCE: 12

His His Gln Lys Leu Val Phe
 1               5

<210> SEQ ID NO 13
<211> LENGTH: 7
<212> TYPE: PRT
<213> ORGANISM: Amyloidosis

<400> SEQUENCE: 13

Val His His Gln Lys Leu Val
 1               5

```
<210> SEQ ID NO 14
<211> LENGTH: 7
<212> TYPE: PRT
<213> ORGANISM: Amyloidosis

<400> SEQUENCE: 14

Glu Val His His Gln Lys Leu
 1               5

<210> SEQ ID NO 15
<211> LENGTH: 6
<212> TYPE: PRT
<213> ORGANISM: Amyloidosis

<400> SEQUENCE: 15

His Gln Lys Leu Val Phe
 1               5

<210> SEQ ID NO 16
<211> LENGTH: 6
<212> TYPE: PRT
<213> ORGANISM: Amyloidosis

<400> SEQUENCE: 16

His His Gln Lys Leu Val
 1               5

<210> SEQ ID NO 17
<211> LENGTH: 6
<212> TYPE: PRT
<213> ORGANISM: Amyloidosis

<400> SEQUENCE: 17

Val His His Gln Lys Leu
 1               5

<210> SEQ ID NO 18
<211> LENGTH: 6
<212> TYPE: PRT
<213> ORGANISM: Amyloidosis

<400> SEQUENCE: 18

Glu Val His His Gln Lys
 1               5

<210> SEQ ID NO 19
<211> LENGTH: 5
<212> TYPE: PRT
<213> ORGANISM: Amyloidosis

<400> SEQUENCE: 19

Gln Lys Leu Val Phe
 1               5

<210> SEQ ID NO 20
<211> LENGTH: 5
<212> TYPE: PRT
<213> ORGANISM: Amyloidosis

<400> SEQUENCE: 20

His Gln Lys Leu Val
 1               5

<210> SEQ ID NO 21
<211> LENGTH: 5
```

```
<212> TYPE: PRT
<213> ORGANISM: Amyloidosis

<400> SEQUENCE: 21

His His Gln Lys Leu
  1               5

<210> SEQ ID NO 22
<211> LENGTH: 5
<212> TYPE: PRT
<213> ORGANISM: Amyloidosis

<400> SEQUENCE: 22

Val His His Gln Lys
  1               5

<210> SEQ ID NO 23
<211> LENGTH: 5
<212> TYPE: PRT
<213> ORGANISM: Amyloidosis

<400> SEQUENCE: 23

Glu Val His His Gln
  1               5

<210> SEQ ID NO 24
<211> LENGTH: 4
<212> TYPE: PRT
<213> ORGANISM: Amyloidosis

<400> SEQUENCE: 24

Leu Val Phe Phe
  1

<210> SEQ ID NO 25
<211> LENGTH: 4
<212> TYPE: PRT
<213> ORGANISM: Amyloidosis

<400> SEQUENCE: 25

Lys Leu Val Phe
  1

<210> SEQ ID NO 26
<211> LENGTH: 4
<212> TYPE: PRT
<213> ORGANISM: Amyloidosis

<400> SEQUENCE: 26

Gln Lys Leu Val
  1

<210> SEQ ID NO 27
<211> LENGTH: 4
<212> TYPE: PRT
<213> ORGANISM: Amyloidosis

<400> SEQUENCE: 27

His Gln Lys Leu
  1

<210> SEQ ID NO 28
<211> LENGTH: 4
<212> TYPE: PRT
<213> ORGANISM: Amyloidosis
```

```
<400> SEQUENCE: 28

His His Gln Lys
  1

<210> SEQ ID NO 29
<211> LENGTH: 4
<212> TYPE: PRT
<213> ORGANISM: Amyloidosis

<400> SEQUENCE: 29

Val His His Gln
  1

<210> SEQ ID NO 30
<211> LENGTH: 4
<212> TYPE: PRT
<213> ORGANISM: Amyloidosis

<400> SEQUENCE: 30

Glu Val His His
  1

<210> SEQ ID NO 31
<211> LENGTH: 3
<212> TYPE: PRT
<213> ORGANISM: Amyloidosis

<400> SEQUENCE: 31

Val Phe Phe
  1

<210> SEQ ID NO 32
<211> LENGTH: 3
<212> TYPE: PRT
<213> ORGANISM: Amyloidosis

<400> SEQUENCE: 32

Leu Val Phe
  1

<210> SEQ ID NO 33
<211> LENGTH: 3
<212> TYPE: PRT
<213> ORGANISM: Amyloidosis

<400> SEQUENCE: 33

Lys Leu Val
  1

<210> SEQ ID NO 34
<211> LENGTH: 3
<212> TYPE: PRT
<213> ORGANISM: Amyloidosis

<400> SEQUENCE: 34

Gln Lys Leu
  1

<210> SEQ ID NO 35
<211> LENGTH: 3
<212> TYPE: PRT
<213> ORGANISM: Amyloidosis

<400> SEQUENCE: 35
```

```
His Gln Lys
  1

<210> SEQ ID NO 36
<211> LENGTH: 3
<212> TYPE: PRT
<213> ORGANISM: Amyloidosis

<400> SEQUENCE: 36

His His Gln
  1

<210> SEQ ID NO 37
<211> LENGTH: 3
<212> TYPE: PRT
<213> ORGANISM: Amyloidosis

<400> SEQUENCE: 37

Val His His
  1

<210> SEQ ID NO 38
<211> LENGTH: 3
<212> TYPE: PRT
<213> ORGANISM: Amyloidosis

<400> SEQUENCE: 38

Glu Val His
  1

<210> SEQ ID NO 39
<211> LENGTH: 5
<212> TYPE: PRT
<213> ORGANISM: Amyloidosis

<400> SEQUENCE: 39

Ala Leu Val Phe Phe
  1               5

<210> SEQ ID NO 40
<211> LENGTH: 5
<212> TYPE: PRT
<213> ORGANISM: Amyloidosis

<400> SEQUENCE: 40

Lys Ala Val Phe Phe
  1               5

<210> SEQ ID NO 41
<211> LENGTH: 5
<212> TYPE: PRT
<213> ORGANISM: Amyloidosis

<400> SEQUENCE: 41

Lys Leu Ala Phe Phe
  1               5

<210> SEQ ID NO 42
<211> LENGTH: 5
<212> TYPE: PRT
<213> ORGANISM: Amyloidosis

<400> SEQUENCE: 42

Lys Leu Val Ala Phe
```

-continued

```
                1               5

<210> SEQ ID NO 43
<211> LENGTH: 5
<212> TYPE: PRT
<213> ORGANISM: Amyloidosis

<400> SEQUENCE: 43

Lys Leu Val Phe Ala
 1               5

<210> SEQ ID NO 44
<211> LENGTH: 8
<212> TYPE: PRT
<213> ORGANISM: Amyloidosis

<400> SEQUENCE: 44

Lys Leu Val Phe Phe Ala Ala Cys
 1               5
```